United States Patent [19]

Swaringen, Jr. et al.

[11] Patent Number: 4,761,418
[45] Date of Patent: Aug. 2, 1988

[54] NOVEL COMPOUNDS

[75] Inventors: Roy A. Swaringen, Jr., Durham, N.C.; Hassan A. El-Sayad, Nasr City, Egypt; David A. Yeowell, Chapel Hill, N.C.; John J. Savarese, Boxford, Mass.

[73] Assignees: Burroughs Wellcome Co., Research Triangle Park, N.C.; General Hospital Corporation, Boston, Mass.

[21] Appl. No.: 756,025

[22] Filed: Jul. 17, 1985

[30] Foreign Application Priority Data

Jul. 18, 1984 [GB] United Kingdom ............... 8418303

[51] Int. Cl.$^4$ ..................... A61K 31/47; C07C 401/14
[52] U.S. Cl. ....................................... 514/308; 546/140
[58] Field of Search .................... 546/140; 514/308

[56] References Cited

U.S. PATENT DOCUMENTS

| | | | |
|---|---|---|---|
| 3,004,031 | 10/1961 | Taylor et al. | 546/140 |
| 4,179,507 | 12/1979 | Stenlake et al. | 546/140 |
| 4,192,877 | 3/1980 | Savarese et al. | 546/140 |
| 4,235,906 | 11/1980 | Savarese et al. | 546/140 |
| 4,491,665 | 1/1985 | El-Sayad et al. | 546/140 |

FOREIGN PATENT DOCUMENTS

| | | |
|---|---|---|
| 0010119 | 4/1980 | European Pat. Off. . |
| 0054309 | 6/1982 | European Pat. Off. . |
| 0080682 | 6/1983 | European Pat. Off. . |
| 863717 | 3/1961 | United Kingdom . |
| 2002758A | 2/1979 | United Kingdom . |
| 2061929B | 5/1981 | United Kingdom . |
| 2061929A | 5/1981 | United Kingdom . |

OTHER PUBLICATIONS

The Alkaloids, vol. X, 1968, pp. 402–403, 424–428.
Recherches Sur Les Poisons Curarisants De Synthese, Bovet et al., 1951.
Br. J. Pharmac., (1972), 44, 765–778.
J. Chem. Soc. Perkin Trans., 1, 1982, pp. 1068-2077.
J. Chem. Soc. (C), 1966, S. M. Albonico et al.
Brit. J. Pharmacol., (1961), 17, 116–123.
Chem. Abstracts, vol. 71, 1969.
J. Chem. Soc., Gladych and Taylor, (1962).

Primary Examiner—Glennon H. Hollrah
Assistant Examiner—James H. Turnipseed
Attorney, Agent, or Firm—Donald Brown

[57] ABSTRACT

Neuromuscular blocking agents of formula (1) which are useful as skeletal muscle relaxants during surgery are disclosed.

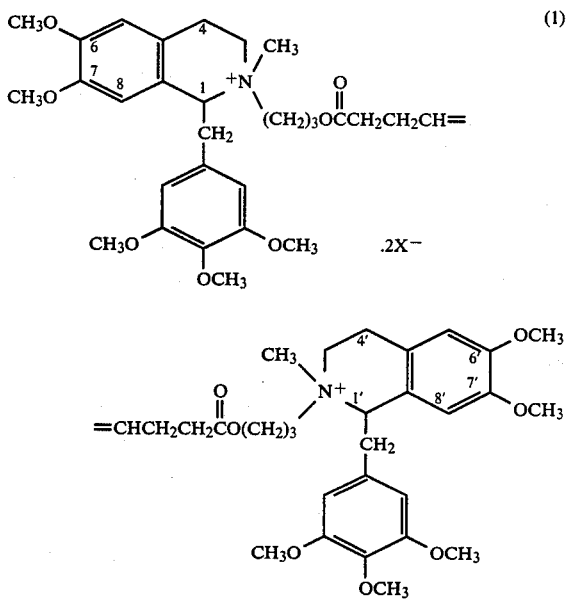

and X is an anion, preferably pharmaceutically acceptable.

15 Claims, No Drawings

NOVEL COMPOUNDS

The present invention relates to novel compounds, method for the preparation of such compounds, pharmaceutical compositions containing them and their use in human and veterinary medicine as neuromuscular blocking agents of short duration.

In anesthesia, neuromuscular blocking agents are used to provide skeletal muscle relaxation during surgery and during intubation of the trachea. Neuromuscular blocking agents are used in practically every field of surgery.

In general there are two types of neuromuscular blocking agents in use, non-depolarizing and depolarizing.

The non-depolarizing agents include the long duration agents d-tubocurarine, pancuronium, gallamine, diallyltoxiferine, toxiferine, and the intermediate duration agents atracurium and vecuronium.

The depolarizing agents include succinylcholine and decamethonium. All the conventional non-depolarizing agents when used for producing skeletal muscle relaxation in surgery have a long duration of action, e.g. 60 to 180 minutes in humans. The conventional depolarizing agents, on the other hand, provide muscle relaxation with duration of action shorter than that of the non-depolarizing agents. For example, succinylcholine provides a short duration of action of about 5 to 15 minutes of muscle relaxation in humans.

The long-duration non-depolarizing agents have inherent side effects. For example, gallamine and pancuronium may cause tachycardia, and d-tubocurarine and diallyltoxiferine may cause hypotension. The intermediate duration and long duration non-depolarizing agents lack a rapid onset of neuromuscular paralysis.

While these non-depolarizing agents can be pharmacologically antagonized with anticholinesterase agents, this may necessitate the administration of a second drug which itself may have its own side effects, e.g., bradycardia, gut spasm and bronchorrhea. Thus, to overcome the aforementioned side effects of the anticholinesterase agents, a third drug, an anticholinergic agent, e.g., atropine, may also be given.

The only short-duration agent currently available for therapeutic use is the depolarizing agent, succinylcholine. The depolarizing agents to the best of the applicant's knowledge have no pharmacological antagonists and therefore cannot be reversed in patients who get into difficulty or if quicker recovery is desired. While in most cases there is no need to reverse the effects of the depolarizing agents, in certain patients the effects of succinylcholine are much prolonged because of abnormal metabolism of the agent by the patient.

The depolarizing agents due to their mode of action initially cause skeletal muscle contraction and stimulation of smooth muscles also cause the following side effects in certain instances: increased intraocular pressure, and intragastric tension, cardiac arrhythmias, potassium release and muscle pain.

These side effects caused by the depolarizing agents are not caused by the non-depolarizing agents. It is, therefore, clearly evident, and indeed has been recognized by clinicians for over 25 years, that a neuromuscular blocking agent which would combine the short duration of the depolarizing agents with the relatively few side effects and the pharmacologic reversibility of the non-depolarizing agents would be beneficial.

It has now been discovered that novel compounds of the formula (1) are potent neuromuscular blocking agents of relatively short duration, e.g., about ten minutes in monkeys. These compounds have a non-depolarising mechanism of action, are pharmacologically reversible and have a relatively rapid onset of action, a feature which is of great importance in emergency surgical procedures.

Accordingly, the present invention provides compounds of the formula (1):

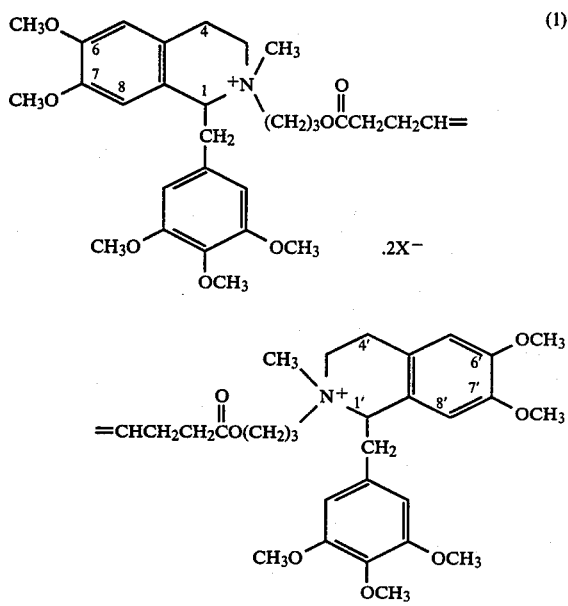

wherein $X^-$ is an anion.

The compounds of formula (1) contain a chiral center at the C(1) and C(1') carbon atoms of the isoquinolinium moieties and, therefore, may either the R or the S configuration exist at each center. The R configuration is that obtained using (−)-5'-methoxylaudanosine, also identified as (R)-(−)-5'-methoxylaudanosine, the preparation of which is described in the Example section. The compounds of formula (1) having the R configuration at both chiral centers are essentially free from significant side effects at the dosages that it is anticipated will be used clinically whereas the corresponding enantiomeric compounds, i.e., those having the S configuration at both centers, are likely to induce adverse cardiovascular effects, such as those associated with histamine release at clinically useful dosages. Accordingly, the compounds of formula (1), wherein the configuration at both the C(1) and the C(1') carbon atoms is the R configuration, constitute a preferred sub-class.

The compounds of formula (1) also contain an alkenic double bond and may, therefore, exist in either the E or the Z configuration, for example the E configuration. Moreover, the substituents about each of the quaternary nitrogen atoms may exist in either the R or the S configuration as well. As a result, for each of the geometric isomers (E or Z) of the preferred sub-class of compounds of formula (1) wherein the configuration at the C(1) and C(1') carbon atoms is the R configuration there are three diastereomers, the RR-RR, RS-RS and RR-RS. The RS-RR diastereomer is equivalent to the RR-RS Diastereomer thus, there are a total of six. The present invention extends to these six diastereoisomers individually and as mixtures.

Within each set of diastereomers, the most potent are those having the RS-RS and the RS-RR configurations and are surprisingly more potent than the RR-RR diastereomers. However, the preferred embodiment within the scope of formula (1) in terms of potency and cost of manufacture is not any single diastereomer but the mixture of all three diastereomers. Within such a mixture, it is preferred that the RS-RS and RR-RS diastereomers together constitute the greater part, especially greater than 70% or even 80% or 90% (w/w). In fact, it is even more preferred that the mixture comprises from 1 to 15% (w/w) of the RR-RR diastereomer, from 38 to 50% (w/w) of the RR-RS diastereomer and from 40 to 56% (w/w) of the RS-RS diastereomer.

Since the pharmacological activity of the compounds of the invention resides in the di-cation, the nature of the anion $X^-$ is relatively unimportant, although for therapeutic purposes it is, preferably, pharmaceutically acceptable to the recipient of the compounds. Examples of pharmaceutically acceptable anions include iodide, mesylate, tosylate, bromide, chloride, hydrogen sulphate, sulphate/2, phosphate/3, hydrogen phosphate/2, acetate, benzenesulphonate, hemisuccinate, succinate/2, maleate, naphthalenesulphonate and propionate. The pharmacologically acceptable salts together with the salts which are not thus acceptable have utility in the isolation and/or purification of the compounds of the invention, and the unacceptable salts are also useful in being convertible into the acceptable salts by techniques well known in the art.

The compounds of formula (1) are used as neuromuscular blocking agents in conjuction with surgery or for intubation of the trachea by conventional parenteral administration, e.g., intramuscular or intravenous administration in solution. Accordingly, the present invention also provides a method for producing muscle relaxation in a mammal, which comprises administering to the mammal an effective neuromuscular blocking amount of a compound of formula (1). In the alternative, there is provided a compound of formula (1) for use in human or veterinary medicine, especially for producing muscle relaxation in mammals. The compounds of the present invention are administered to subjects such as monkeys and humans and other mammals to achieve neuromuscular blockade. The dosage for each type of subject will vary because of the peculiarities of the species. However, a suitable intravenous amount or dosage of the compounds of formula (1) to obtain paralysis in mammals would be 0.01 to 0.50 mg/kg of body weight, and most preferably, 0.025 to 0.3 mg/kg of body weight, the above being based on the weight of the di-cation which is the active ingredient. The dosage for intramuscular administration is two to four times the intravenous dose. The compounds of this invention are reversible using conventional anticholinesterase agents such as neostigmine and edrophonium and appear to avoid the side effects associated with the conventional non-depolarizing agents.

The compounds of formula (1) are therefore useful for producing a short duration neuromuscular blockade in humans as well as in other mammals, and the present invention provides a method of producing such blockade in mammals by intravenously injecting a dose of 0.01 to 0.50 mg/kg to the mammal. It should be understood that the profile of neuromuscular blockade in a mammal such as monkey is similar to humans and the compounds of formula (1) are considered as a short duration agent for the monkey.

While it is possible for compounds of formula (1) to be administered as the bulk active chemicals, it is preferred to present them in the form of a pharmaceutical formulation, in particular a pharmaceutical formulation for parenteral administration. Accordingly, the present invention provides a pharmaceutical formulation which comprises a compound of formula (1), as herein defined, and a pharmaceutically acceptable carrier.

In the preferred case where the pharmaceutical formulation is for parenteral administration, the formulation may be an aqueous or non-aqueous solution or emulsion in a pharmaceutically acceptable liquid or mixture of liquids, which may contain bacteriostatic agents, antioxidants, buffers, thickening agents, suspending agents or other pharmaceutically acceptable additives. Alternatively the compounds may be presented as lyophilized solids for reconstitution with water (for injection) or dextrose or saline solutions. Such formulations are normally presented in unit dosage forms such as ampoules or disposable injection devices, or in multidose forms such as a bottle from which the appropriate dose may be withdrawn; all such formulations should be sterile.

The suitable unit dose to obtain a neuromuscular block for adult humans ($-150$ lbs or 70 kg) is 0.5 to 30 mg and most preferably 3.5 to 15 mg.

The compounds of this invention if desired may be administered in conjunction with depolarizing agents such as listed above.

Thus a suitable pharmaceutical parenteral preparation for administration to humans will preferably contain 0.1 to 5 mg/ml of the compounds of formula (1) of this invention in solution or multiples thereof for multidose vials.

A simple and preferred formulation is a solution of the compound of formula (1) in water or dextrose solution which may be prepared by simply dissolving the compound in pyrogen-free water or water containing dextrose, with or without a preservative and sterilizing the solution, or by dissolving the sterile compound in pyrogen-free, sterile water or a sterile dextrose solution under aseptic conditions.

The compounds of formula (1) may also be administered as an infusion of a dextrose solution or a saline solution, e.g., Ringer's solution, in drip form.

The compounds may also be administered in other solvents (usually as a mixed solvent with water) such as alcohol, polyethylene glycol and dimethylsulphoxide. They may also be administered intramuscularly (as a drip if required) as a suspension or solution.

The compounds of formula (1) may be prepared by coupling a compound of formula (2):

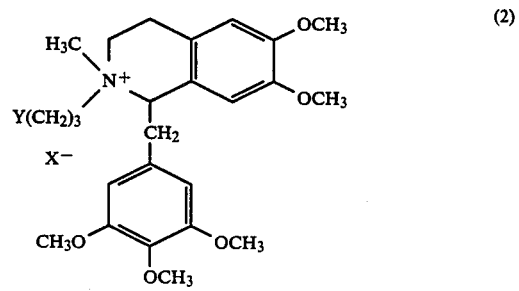

(2)

wherein X⁻ is as defined hereinafter and Y can be hydroxy, chloro, bromo, iodo, or tosyloxy, with a compound of formula (3):

ZOCCH₂CH₂CH=CHCH₂CH₂COZ  (3)

wherein Z is hydroxy, chloro, bromo or C₁₋₄ alkylcarbonyloxy, preferably chloro. At least one of Y and Z is always hydroxy.

The coupling between the compounds of formulae (2) and (3) may be carried out conventionally, for example, by stirring a solution of the compounds, in which the compound of formula (2) is present in excess, in a solvent, such as 1,2-dichloroethane, at ambient or an elevated temperature.

The geometric configuration of the compound of formula (1) resulting from the coupling between the compounds of formulae (2) and (3) corresponds to the geometric configuration of the compound of formula (3). Thus, in order to obtain a compound of formula (1) with, say, the E-configuration, then the compound of formula (3) should also have the E-configuration.

The compound of formula (1), as obtained from the coupling between the compounds of formulae (2) and (3), is usually in the form of a mixture of optical isomers in which the RS-RS and the RR-RS optical isomers together account for the greater part of the mixture. If desired, one or more diastereomers can be separated from the mixture using conventional techniques for example chromatographic techniques.

The compound of formula (2) may be prepared by reacting a compound of formula (4):

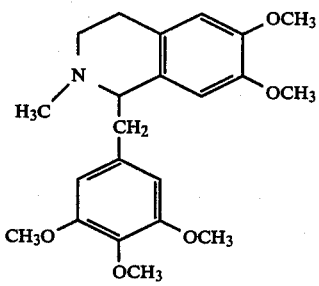

with a compound of formula (5):

X—(CH₂)₃—OH  (5)

wherein X corresponds to the anion, X⁻, defined hereinbefore; and optionally converting the anion X⁻ in the resulting compound of formula (2) into another anion.

The reaction between the compounds of formulae (4) and (5) is, preferably, carried out conventionally, for example, under reflux in a solvent, such as 2-butanone, in the presence of a base, such as sodium carbonate.

Preferably, X, in the compound of formula (5), is iodo, the compound being formed in situ from the corresponding compound of formula (5), wherein X is chloro, and sodium iodide.

In the preferred case where X, in the compound of formula (5), is iodo, the anion X⁻ in the compound of formula (2), resulting from the reaction between the compounds of formulae (4) and (5), is an iodide anion. In this case, it is preferred subsequently to convert the iodide anion in the resulting compound of formula (2) into a pharmaceutically acceptable anion, such as the chloride anion, using conventional techniques.

The compounds of formulae (3), (4) and (5) are commercially available, or may be obtained by carrying out a published process for their preparation, or by carrying out a process analogous to a published process for the preparation of structurally analogous compounds.

The reached compounds of formula (2), on the other hand, are novel intermediates of use in the preparation of the compounds of formula (1), and, therefore, represent part of the present invention.

The present invention will now be described by reference to specific embodiments thereof.

GENERAL COMMENTS

All solvents and chemicals used were reagent grade and used without further purification. Analytical HPLC, unless otherwise noted, was performed on a Whatman Partisil 10 w (25 cm × 4.6 mm) column using a 20 μl sampling loop. The mobile phase used was methanol:ethyl acetate:trifluoroacetic acid:sulfuric acid: 61.1:38.5:0.3:0.1 at a flowrate of 2 mL/min. Detection was at 280 nm. While retention times (RT) vary with a number of factors, the order of elution is:

| COMPOUNDS | RT |
| --- | --- |
| (E)—(1R,2R)—2-[3-[(7-Carboxy-4-heptenoyl)oxy]propyl]-6,7-dimethoxy-2-methyl-1-(3,4,5-trimethoxybenzyl)-isoquinolinium chloride | 150 sec |
| (E)—(1R,2S)—2-[3[(7-Carboxy-4-heptenoyl)oxy]propyl]-6,7-dimethoxy-2-methyl-1-(3,4,5-trimethoxybenzyl)-isoquinolinium chloride | 203 sec |
| cis-1,2,3,4-Tetrahydro-2-(3-hydroxypropyl)-6,7-dimethoxy-2-methyl-1-(3,4,5-trimethoxybenzyl)isoquinolinium chloride | 250 sec |
| trans-1,2,3,4-Tetrahydro-2-(3-hydroxypropyl)-6,7-dimethoxy-2-methyl-1-(3,4,5-trimethoxybenzyl)isoquinolinium chloride | 315 sec |
| 2,2'[(E)—4-Octenedioylbis(oxytrimethylene)]bis[1R,2R—1,2,3,4-tetrahydro-6,7-dimethoxy-2-methyl-1-(3,4,5-trimethoxybenzyl)isoquinolinium] dichloride | 357 sec |
| (E)—(1R,1'R,2R,2'S)—2,2'-[4-Octenedioylbis(oxytrimethylene)]bis[1,2,3,4-tetrahydro-6,7-dimethyoxy-2-methyl-1-(3,4,5-trimethoxybenzyl)isoquinolinium] dichloride | 519 sec |
| 2,2'-[(E)—4-Octenedioylbis(oxytrimethylene)]bis[(1R,2S)—1,2,3,4-tetrahydro-6,7-dimethoxy-2-methyl-1-(3,4,5-trimethoxybenzyl)isoquinolinium] dichloride | 751 sec |

All diesters were dried to constant weight at 0.1 mm Hg pressure and ambient temperature. Rotations are calculated on a volatiles-free basis.

EXAMPLE 1

2,2'[(E)-4-Octenedioylbis(oxytrimethylene)]bis[(trans)-1,2,3,4-tetrahydro-6,7-dimethoxy-2-methyl-1-(3,4,5-trimethoxybenzyl)isoquinolinium]dichloride a. Compound A:

trans-1,2,3,4-Tetrahydro-2-(3-hydroxypropyl)-6,7-dimethoxy-2-methyl-1-(3,4,5-trimethoxybenzyl-)isoquinolinium chloride (trans quaternary chloride)

5'-Methoxylaudanosine (4.6 g), 3-chloropropanol (2.2 g), sodium iodide 3.5 g) and sodium carbonate (0.3 g) were refluxed in 2-butanone (45 mL) for 24 h. The white suspension was filtered hot and solvent was removed under vacuum. The resulting gum was triturated with diethyl ether to remove excess 3-iodopropanol. Residual solvent was removed under vacuum to give an amorphous solid which was assayed by HPLC as 6.3/1, trans/cis quaternary iodide salt. The material was dissolved in H₂O (45 mL), cooled to 0° C. and filtered to remove the precipitated cis isomer. Conversion to the chloride salt was accomplished by passing the trans enriched liquors through a column packed with Dowex®1-X8 ion exchange resin (35 g). The eluant was concentrated under vacuum. Acetone trituration of the residual oil gave the chloride salt as a white solid. Slurrying the solids in dry N,N-dimethylformamide (20 mL) at 80° C. for 10 minutes removed the last traces of the cis isomer. The material was slurried in hot acetone to remove residual N,N-dimethylformamide and filtered to give 4.8 g (84%) of the quaternary chloride which was assayed by HPLC as 100% trans isomer: mp 212°–213° C.

Confirmation of the trans orientation was obtained by X-ray crystallographic analysis of the perchlorate salt of Compound A and reported in J. Chem. Soc. Perkin Trans I, 2067 (1982).

Calculated for $C_{25}H_{36}NO_6Cl$: C, 62.30; H, 7.53; N, 2.90; Cl, 7.36. Found: C, 62.35; H, 7.52; N, 2.91; Cl, 7.32.

b. Compound B:
cis-1,2,3,4-Tetrahydro-2-(3-hydroxypropyl)-6,7-dimethoxy-2-methyl-1-(3,4,5-trimethoxybenzyl)isoquinolinium iodide (cis quaternary iodide)

5'-Methoxylaudanosine (47 g) and 3-iodopropanol (45 g) were refluxed in acetonitrile (500 mL) for 18 h. The solvent was removed under vacuum. The resulting gum was triturated with diethyl ether to remove excess 3-iodopropanol. Residual solvent was removed under vacuum to give an orange oil which was assayed by HPLC as 3/1, trans/cis quaternary iodide salt. The oil was dissolved in acetone (200 mL) and cooled at −5° C. for 18 h. The solid was filtered and dried for 2 h at 50° C. giving 37.1 g of the quaternary iodide mixture (3:1 trans:cis by HPLC). The solid was triturated with water (200 mL) and filtered giving 10.5 g of purified cis quaternary iodide. Recrystallization from acetonitrile provided 7.7 g (11%) of white, crystalline solid: mp 142°–144° C.

Confirmation of the cis orientation was obtained by x-ray crystallographic analysis of Compound B and reported in J. Chem. Soc., Ibid.

Calculated for $C_{25}H_{36}NO_6I·H_2O$: C, 50.80; H, 6.42; N, 2.36. Found: C, 50.74; H, 6.51; N, 2.34.

c. Compound C:
2,2'-[(E)-4-Octenedioylbis(oxytrimethylene)]bis[(trans)-1,2,3,4-tetrahydro-6,7-dimethoxy-2-methyl-1-(3,4,5-trimethoxybenzyl)isoquinolinium]dichloride Trans-N-3-hydroxypropyl-5'-methoxylaudanosinium chloride (100% trans by HPLC, 5.9 g) was suspended in 80 ml 1,2-dichloroethane at −70° C. (E)-4-octene-1,8-dioic acid chloride (1.2 g) (K. Sisido, K. Sei, H. Nozaki; *J. Org. Chem.*, 1962, 27, 2681) was added and the mixture was stirred at ambient temperature for 72 h. The reaction mixture was filtered and solvent was removed under vacuum to give an amorphous solid which was suspended in 1% aqueous sodium chloride solution. The suspension was adjusted to pH 8.0 with 1% sodium hydroxide and extracted with chloroform (3×200 mL). The combined chloroform extracts were evaporated to dryness. The residue was again suspended in 1% aqueous sodium chloride and the neutralization-extraction process was repeated as before. The combined chloroform portions were dried over anhydrous calcium chloride and filtered. The filtrate was evaporated to dryness. The residue was dissolved in 100 mL ethanol and evaporated to a foam which was further evaporated to constant weight under high vacuum (0.5 mm Hg). The white solid (2.8 g, 41%) was found to be 95% pure by HPLC.

Calculated for $C_{58}H_{80}N_2O_{14}Cl_2·5.1H_2O$: C, 58.44; H, 7.63; N, 2.21; Cl, 5.95. Found: C, 58.17; H, 7.34; N, 2.35; Cl, 6.07.

EXAMPLE 2

(+−)trans, trans-2,2'-(Z)-4-Octenedioylbis(oxytrimethylene))-bis(1,2,3,4-tetrahydro-6,7-dimethoxy-2-methyl-1-(3,4,5-trimethoxybenzyl)isoquinolinium dichloride
Compound D Trans-N-3-hydroxypropyl-5'-methoxylaudanosinium chloride (Compound A, 100% trans by HPLC, 5.88 g) was suspended in 80 ml 1,2-dichloroethane at 70° C. and (Z)-4-Octene-1,8,-dioic acid chloride (1.2 g) was added. (A. Manzocchi, F. Astori, E. Sontaniello; *Synthesis*, 1983, 324. The diacid chloride was prepared as in Example 1). The mixture was stirred at ambient temperature for 16 h and filtered. The filtrate was concentrated to a foam and partitioned between water (65 mL) and nitromethane (15 mL). The aqueous portion was washed with diethyl ether and treated with sodium chloride (1.6 g). The brine solution was extracted with chloroform (40 mL). The chloroform extract was concentrated to a gum and subsequently dissolved in 2.5% aqueous sodium chloride solution (65 mL). The pH was adjusted to 9.0 with 0.1M sodium hydroxide and the aqueous solution extracted with chloroform (40 mL). The chloroform solution was washed with 5% aqueous sodium chloride (20 mL), dried over anhydrous calcium chloride, filtered and evaporated to a residue under reduced pressure. The solid was dissolved in ethanol (95%) and evaporated back down to a foam under reduced pressure. The foam was brought to constant weight under vacuum (0.5 mm Hg) giving 4.0 g (57%) of Compound D (92.2% by HPLC).

Calculated for $C_{58}H_{80}N_2O_{14}Cl_2·5.8H_2O$: C, 57.78; H, 7.69; N, 2.33; Cl, 5.89. Found: C, 57.83; H, 7.66; N, 2.33; Cl, 5.89.

EXAMPLE 3

(E)-(1R,1'R)-2,2'-[4-Octenedioylbis(oxytrimethylene)]-bis[1,2,3,4-tetrahydro-6,7-dimethoxy-2-methyl-1-(3,4,5-trimethoxybenzyl)isoquinolinium]dichloride
(Compound G)

a. Compound E: (R)-(−)-5'-Methoxylaudanosine

To (±)-5'-methoxylaudanosine (46.4 g) in methanol (240 mL) was added (−)-dibenzoyltartaric acid monohydrate (45.2 g). The mixture was heated to boiling, cooled at 5° C. for 16 h and the (S)-(−)-5'-methoxylaudanosinium dibenzoyltartrate salt (35.6 g, 80%) was filtered and discarded. The mother liquors were made basic with concentrated aqueous NaOH and evaporated under vacuum. The solid residue was partitioned between H₂O (200 mL) and diethyl ether (2×150 mL). The ether phase was dried and evaporated to an oil (24.9 g). To the oil in methanol (128 mL) was added (+)-dibenzoyltartaric acid monohydrate (26.6 g). The mixture was heated to boiling and cooled at 5° C. for 16 h. Crystals were collected and recrystallized from methanol until a constant specific rotation of $[\alpha]_D^{20} = +17.7°$ (1% EtOH) had been achieved. The yield of (R)-(+)-5'-methoxylaudanosinium dibenzoyltartrate as white crystals was 29.4 g (66%). A portion of the salt (15.0 g) in methanol (200 mL) was made basic with concentrated aqueous NaOH. The mixture was evaporated under vacuum and the residue was partitioned between H$_2$O (200 mL) and diethyl ether (2×200 mL). The combined ether layers were dried and evaporated under vacuum to yield 7.2 g (92%) of (R)-(−)-5′-methoxylaudanosine as an oil.

b. Compound F (R)-(−)-5′-Methoxylaudanosine (7.2 g), 3-chloropropanol (3.5 g), sodium iodide (5.6 g) and sodium carbonate (0.5 g) were refluxed in 2-butanone (125 mL) for 16 h. The white suspension was filtered hot and solvent removed from the filtrate under vacuum. The residual gum was triturated with hot ethyl acetate to remove excess 3-iodopropanol, dissolved in 200 mL methanol and passed through a column packed with Dowex ®1-X8 ion exchange resin (60 g chloride form). The eluant was stripped of solvent under vacuum to give the quaternary chloride salt (8.4 g) as an amophous solid. The material was assayed by HPLC as a 2.3/1 mixture of the trans/cis diastereomers.

c. Compound G

N-3-Hydroxypropyl-1-(R)-5′-methoxylaudanosinium chloride (2.3/1, trans/cis by HPLC, 2.5 g) was dissolved in 60 mL 1,2-dichloroethane at about 70° C. (E)-4-Octene-1,8-dioic acid chloride (0.5 g) (K. Sisido, K. Sei, and H. Nozaki, *J. Org. Chem.*, 1962, 27, 2681) was added and the mixture was stirred at ambient temperature for 19 h. Solvent was removed under vacuum to give an amorphous solid which was dissolved in chloroform (25 mL) and washed with 5% aqueous sodium chloride solution (3×35 mL) to remove unreacted quaternary salts. The chloroform layer was dried and evaporated under vacuum to give an amorphous solid. The acid ester impurities were substantially removed by washing with hot 2-butanone. Residual solvent was evaporated under vacuum and the resulting amorphous solid was dissolved in methanol, filtered and lyophilized to give 1.9 g of (E)-(1R,1′R)-2,2′-[4-octenedioylbis(oxytrimethylene)]-bis[1,2,4,3-tetrahydro-6,7-dimethoxy-2-methyl-1-(3,4,5-trimethoxybenzyl)isoquinolinium]dichloride, Compound G, which was assayed by HPLC as 44.6% RS-RS (trans-trans) diester, 42.4% RR-RS (cis-trans) diester, 7.5% RR-RR(cis-cis) diester, 4.0% RS (trans) acid ester and 1.5% RR (cis) acid ester. $[\alpha]_D^{20} = -62.7°$ (1.9% in H$_2$O).

Calculated for C$_{58}$H$_{80}$N$_2$O$_{14}$.2Cl.4H$_2$O: C, 59.44; H, 7.57; N, 2.39; Cl, 6.05. Found: C, 59.36; H, 7.60; N, 2.36; Cl, 5.99.

EXAMPLE 4

Chromatographic Separation of the Individual Components of Compound G a.

A Waters HPLC/System 500A (Waters Associates, Milford, MA 01757) fitted with two silica gel cartridges in tandem was employed in this separation. The columns were pre-equilibrated in the mobile phase (ethanol:methanol:tetramethyl ammonium chloride: 600:400:1) and the diester mixture (Compound G, 5 g) in ethanol (25 ml) was loaded on the column. The system was eluted with 13.2 l of mobile phase which was collected in 66 fractions (200 ml). The fractions were analyzed by analytical HPLC and combined as follows:

b. Compound H (E)-(1R,1′R,2R,2′R)-2,2′-[4-Octenedioylbis(oxytrimethylene)]bis[1,2,3,4-tetrahydro-6,7-dimethoxy-2-methyl-1-(3,4,5-trimethoxybenzyl)isoquinolinium]dichloride Fractions 26–30 were combined and evaporated under reduced pressure. The resultant residue was triturated with chloroform (200 mL) and filtered. The fitrate was washed with 5% aqueous sodium chloride and concentrated to an oil under reduced pressure. The oil was dissolved in ethanol (50 mL) and evaporated to a foam (0.4 g): $[\alpha]_D^{20} = -33.6°$ (1.5% in H$_2$O); $^1$H NMR (CDCl$_3$) from TMS: δ6.64 (s, H5, 2H), 6.27 (s, H2′ and 6′, 4H), 5.75 (s, H8, 2H).

Calculated for C$_{58}$H$_{80}$N$_2$O$_{14}$Cl$_2$, 3.7H$_2$O, 0.9C$_2$H$_5$OH, 0.3 (CH$_3$)$_4$N$^+$Cl$^-$: C, 59.02; H, 7.88; N, 2.62; Cl, 6.61. Found: C, 59.03; H, 7.83; N, 2.60; Cl, 6.57.

Compound H (10 mg) in 1% aqueous phoshoric acid (10 mL) was heated for 18 h at 60°–70° C. and analyzed by HPLC. The cis quaternary salt was observed to the exclusion of the trans quaternary salt. This was verified by co-injections with Compound A and with Compound B.

c. Compound I (E)-(1R,1′R,2R,2′S)-2,2′-[4-Octenedioylbis(oxytrimethylene)]bis[1,2,3,4-tetrahydro-6,7-dimethyoxy-2-methyl-1-(3,4,5-trimethoxybenzyl)isoquinolinium]dichloride Fractions 34–46 were combined and the product isolated in a manner analogous to Compound H. From this was obtained 2.0 g of a white foam: $[\alpha]_D^{20} = -54.0°$ (1.5% in H$_2$O); $^1$H NMR (CDCl$_3$) from TMS: δ6.64 (s, H5, 2H), 6.42 and 6.25 (2s, H2′ and 6′, 4H), 5.75 (s, H8, 2H).

Calculated for C$_{58}$H$_{80}$O$_{14}$Cl$_2$, 1.5H$_2$O, 1.3C$_2$H$_5$OH: C, 61.28; H, 7.76; N, 2.36; Cl, 6.01. Found: C, 61.32; H, 7.71; N, 2.36; Cl, 5.97.

Compound I (10 mg) in 1% aqueous phosphoric acid (10 mL) was heated at 60°–70° C. for 18 h and analyzed by HPLC. Equal amounts of the cis and trans quaternary salts were observed. This was verified by co-injections with Compound A and with Compound B.

d. Compound J (E)-(1R,1′R,2S,2′S)-2,2′-[4-Octenedioylbis(oxytrimethylene)]bis[1,2,3,4-tetrahydro-6,7-dimethoxy-2-methyl-1-(3,4,5-trimethoxybenzyl)isoquinolinium]dichloride Fractions 56–66 were combined and the product isolated in a manner analogous to Compound H. From this was isolated 0.9 g of an off-white foam: $[\alpha]_D^{20} = -76.7°$ [1.5% in H$_2$O]; $^1$H NMR (CDCl$_3$) from TMS: δ6.64 (s, H5, 2H), 6.42 (s, H2′ and 6′, 4H), 5.76 (s, H8, 2H).

Calculated for C$_{58}$H$_{80}$N$_2$O$_{14}$Cl$_2$, 3.3H$_2$O, 1.7C$_2$H$_5$OH, 0.4(CH$_3$)$_4$NCl: C, 59.02; H, 7.99; N, 2.63; Cl, 6.63. Found: C, 59.02; H, 7.99, N, 2.62; Cl, 6.64.

Compound J (10 mg) in 1% aqueous phosphoric acid (10 ml) was heated at 60°–70° C. for 18 hours and analyzed by HPLC. The trans quaternary salt was observed to the exclusion of the cis quaternary salt. This was verified by co-injection with Compound A and with Compound B.

EXAMPLE 5

Biological Activity

The tests employed herein are described by J. J. Savarese (*Anesthesia and Analgesia*, Vol. 52, No. 6, November–December, (1973). Cats were anesthetized with alpha-chloralose (80 mg/kg) and pentobarbital (10 mg/kg) i.p. Monkeys received thiopental (35–40 mg/kg) i.m. followed by halothane (0.5–10% inspired), nitrous oxide (60%) and oxygen (40%) in a nonrebreathing system. In all animals, the trachea was intubated and ventilation was controlled at 12–15 ml/kg, 18–24 breaths per minute. Animals not receiving inhalation anesthetics were ventilated with room air. The left femoral vein and artery were cannulated for drug administration and for recording of arterial pressure, respectively. Square-wave stimuli were applied at supramaximal voltage to the peroneal nerve at 0.15 Hz and the evoked twitches of the tibialis anterior muscle were recorded. Muscle and animal temperatures were maintained between 35° and 38° C. All recordings were made on a Grass Polygraph recorder. The results of these tests are shown in Table I and Table II below.

TABLE I

Direct Comparison of Compound G (diastereomeric Mixture) and Compound J (RS—RS Diastereomer of G) in Cats and Rhesus Monkey

| | CAT[a] | | | RHESUS MONKEY[a] | | |
|---|---|---|---|---|---|---|
| COMPOUND | dose[c] (mg/kg i.v.) | % block | duration[b] (min) | dose (mg/kg/i.v.) | % block | duration (min) |
| G (Example 3c) | 0.04 | 56 ± 12 | 10 ± 2 | 0.02 | 27 | 6 |
| | 0.05 | 78 ± 10 | 13 ± 1 | 0.04 | 99 | 12 |
| J (Example 4d) | 0.04 | 79 ± 4 | 12 ± 2 | 0.02 | 83 | 11 |
| | 0.05 | 96 ± 3 | 12 ± 3 | 0.03 | 100 | 13 |

[a] n = 3 For the cat and n = 1 for the monkey.
[b] The time from intravenous injection to 95% recovery.
[c] Intravenous dose producing 95% neuromuscular paralysis of the tibialis anterior twitch extrapolated from dose-response curves. The ED$_{95}$ neuro-muscular blocking dose is determined because it is related to the degree of muscular paralysis needed to safely facilitate a rapid and easy intubation when neuromuscular blocking agents are used therapeutically.

TABLE II

ED$_{95}$ Values in Cats (Intravenous)

| Compound | Number of Animals | ED$_{95}$ mg/kg[b] |
|---|---|---|
| C | 15 | 0.093 ± 0.005 |
| D | 10 | 0.086 ± 0.010 |
| G | 12 | 0.057 ± 0.005 |
| H | 5 | >0.40 |
| I | 12 | 0.054 ± 0.004 |
| J | 15 | 0.054 ± 0.005 |

[b] The time from intravenous injection to 95% recovery.

Table I shows that in the cat and rhesus monkey Compound G and Compound J have the same neuromuscular blocking profiles except that in both species Compound J is at least 20–25 percent more potent than Compound G.

Table II lists the dose needed to produce 95% neuromuscular blockade (ED$_{95}$) in the animals in the test group for the compounds of formula (1) exemplified herein.

EXAMPLE 6

Toxicity

Three groups of four beagle dogs each were treated twice weekly for three weeks with vehicle, Compound G at five times the ED$_{100}$ or Compound G at fifteen times the ED$_{100}$. Each treatment session consisted of an initial bolus injection followed by a continuous infusion for two hours. All of the dogs were anesthetized with pentobarbital and artificially ventilated during the sessions. All of the dogs survived, and no deleterious effects were observed.

EXAMPLE 7

Formulation

| Injection | Per 5 mL |
|---|---|
| Compound G | 11.0 mg |
| HCl | q.s. pH 4.8 |
| Water (for Injection) | q.s. 5 mL |

The Active Ingredient, i.e. Compound G, is dissolved in 4.8 mL of water (for Injection), aqueous HCl is added to obtain the proper pH and additional water is added to reach a total volume of 5 mL. The resulting solution is filtered through a 2.2 micro meter membrane and sealed in vials or ampules under sterile conditions. Preferably, the formulation is stored under refrigeration (5°–10° C.) until use. Optionally, a preservative may be added to extend shelf life.

We claim:

1. 2,2'[(E)-4-Octenedioylbis(oxytrimethylene)]bis[(-trans)-1,2,3,4-tetrahydro-6,7-dimethoxy-2-methyl-1-(3,4,5-trimethoxybenzyl)isoquinolinium] cation in association with a pharmaceutically acceptable anion.

2. 2,2'-[(E)-4-Octenedioylbis(oxytrimethylene)]bis[(-trans)-1,2,3,4-tetrahydro-6,7-dimethoxy-2-methyl-1-(3,4,5-trimethoxybenzyl)isoquinolinium]dichloride.

3. (+ —)trans,trans-2,2'-(Z)-4-Octenedioylbis(oxytrimethylene))bis-(1,2,3,4-tetrahydro-6,7-dimethoxy-2-methyl-1-(3,4,5-trimethoxybenzyl)isoquinolinium cation in association with a pharmaceutically acceptable anion.

4. (+ —)trans,trans-2,2'-(Z)-4-Octenedioylbis(oxytrimethylene))bis-(1,2,3,4-tetrahydro-6,7-dimethoxy-2-methyl-1-(3,4,5-trimethoxybenzyl)isoquinolinium dichloride.

5. (E)-(1R,1'R)-2,2'-[4-Octenedioylbis(oxytrimethylene)]bis[1,2,3,4-tetrahydro-6,7-dimethoxy-2-methyl-1-(3,4,5-trimethoxybenzyl)isoquinolinium] cation in association with a pharmaceutically acceptable anion.

6. (E)-(1R,1'R)-2,2'-[4-Octenedioylbis(oxytrimethylene)]bis[1,2,4,3-tetrahydro-6,7-dimethoxy-2-methyl-1-(3,4,5-trimethoxybenzyl)isoquinolinium]dichloride.

7. (E)-(1R,1'R,2R,2'R)-2,2'-[4-Octenedioylbis(oxytrimethylene)]bis[1,2,3,4-tetrahydro-6,7-dimethoxy-2-methyl-1-(3,4,5-trimethoxybenzyl)isoquinolinium]cation in association with a pharmaceutically acceptable anion.

8. (E)-(1R,1'R,2R,2'R)-2,2'-[4-Octenedioylbis(oxytrimethylene)]bis[1,2,3,4-tetrahydro-6,7-dimethoxy-2-methyl-1-(3,4,5-trimethoxybenzyl)isoquinolinium]dichloride.

9. (E)-(1R,1'R,2R,2'S)-2,2'-[4-Octenedioylbis(oxytrimethylene)]bis[1,2,3,4-tetrahydro-6,7-dimethoxy-2-methyl-1-(3,4,5-trimethoxybenzyl)isoquinolinium] cation in association with a pharmaceutically acceptable anion.

10. (E)-(1R,1'R,2R,2'S)-2,2'-[4-Octenedioylbis(oxytrimethylene)]bis[1,2,3,4-tetrahydro-6,7-dimethoxy-2-methyl-1-(3,4,5-trimethoxybenzyl)isoquinolinium]chloride.

11. (E)-(1R,1'R,2S,2'S)-2,2'-[4-Octenedioylbis(oxytrimethylene)]bis[1,2,3,4-tetrahydro-6,7-dimethoxy-2-methyl-1-(3,4,5-trimethoxybenzyl)isoquinolinium] dication in association with a pharmaceutically acceptable anion.

12. (E)-(1R,1'R,2S,2'S)-2,2'-[4-Octenedioylbis(oxytrimethylene)]bis[1,2,3,4-tetrahydro-6,7-dimethoxy-2-methyl-1-(3,4,5-trimethoxybenzyl)isoquinolinium]dichloride.

13. A method for producing muscle relaxation in a mammal which comprises parenterally administering to a mammal an effective muscle relaxant amount of the compound of claim 1, 3 or 5.

14. A sterile pharmaceutical composition comprising one or more of the compounds of claims 1, 2, 3, 4, 5, 6, 7, 8, 9, 10, 11 or 12 in an effective muscle relaxant amount and a pharmaceutically acceptable solvent therefor.

15. A method for producing muscle relaxation in a mammal which comprises parenterally administering to a mammal an effective muscle relaxant amount of one or more of the compounds of claims 9, 10, 11 or 12.

* * * * *

UNITED STATES PATENT AND TRADEMARK OFFICE

CERTIFICATE EXTENDING PATENT TERM
UNDER 35 U.S.C. § 156

PATENT NO.: 4,761,418

DATED: August 2, 1988

INVENTORS: Roy A. Swaringen, Jr. et al.

PATENT OWNERS: Burroughs Wellcome Co. and General Hospital Corp.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

173 DAYS with all rights pertaining thereto as provided by 35 U.S.C. § 156(b).

I have caused the seal of the Patent and Trademark Office to be affixed this 20th day of May 1993.

Michael K. Kirk
Acting Commissioner of Patents and Trademarks